United States Patent [19]

Diehl et al.

[11] Patent Number: 4,892,582

[45] Date of Patent: Jan. 9, 1990

[54] DENTAL FILLING-MATERIAL AND METHOD FOR ITS PREPARATION

[75] Inventors: Walter Diehl, Hanau; Hans-Martin Ringelstein, Frankfurt, both of Fed. Rep. of Germany

[73] Assignee: Degussa Aktiengesellschaft, Frankfurt, Fed. Rep. of Germany

[21] Appl. No.: 301,048

[22] Filed: Jan. 24, 1989

[30] Foreign Application Priority Data

Oct. 2, 1988 [DE] Fed. Rep. of Germany ....... 3804022

[51] Int. Cl.$^4$ ............................ C22C 3/00; C22C 5/02
[52] U.S. Cl. ...................................... 75/251; 428/570
[58] Field of Search ................. 75/251, 252, 253, 254, 75/255; 428/570; 106/1018

[56] References Cited

U.S. PATENT DOCUMENTS 1,164,997 12/1915 Davis ................................ 75/251

Primary Examiner—L. Dewayne Rutledge
Assistant Examiner—David W. Schumaker
Attorney, Agent, or Firm—Beveridge, DeGrandi & Weilacher

[57] ABSTRACT

A dental-filling material with hardnesses exceeding 100 HV for gold-condensation is prepared from a gold-alloy powder of which the alloying components are metals resulting in hardening gold alloys and which are simultaneously soluble in nitric acid. A rough, pure gold layer on the surface of the powder particles is obtained by treatment with nitric acid.

5 Claims, No Drawings

DENTAL FILLING-MATERIAL AND METHOD FOR ITS PREPARATION

INTRODUCTION AND BACKGROUND

The present invention relates to a dental-filling material formed of a gold-alloy powder and which can also include an organic binder, to be introduced into tooth cavities using the gold-condensation procedure. In another respect, the present invention relates to a method for preparing this dental-filling material.

The filling of dental cavities with so-called condensed gold is one of the oldest known procedures for filling cavities in teeth. According to this known technology, chemically pure gold in the form of foils, powder or sponge is introduced into the cavity and fastened to it mechanically. In the compacted state, condensed gold has a hardness of about 25 HV which, after being processed by additional cold compaction techniques can be raised to 30 to 50 HV. However, these values are subject to strong local variations depending on the kind of processing, namely, the sort of condensation applied and the various durations of condensation steps. Moreover, because of the temperature effects within the mouth, there is a slow drop-off in the cold compaction. Conventional condensed gold fillings therefore are not well suited for use in situations where it is expected that the filling will be subjected to strong stresses.

In the prior art, German OLS 34 03 779 discloses a dental-filling material for gold condensation purposes consisting of flake gold powder and of a plastic, organic binder liquefying at 20° to 45° C., in particular polyethylene glycol. This material is compacted ultrasonically. The hardnesses so achieved by this known technology, however, are only in the range of 40 HV. The broad application of gold alloys for condensing gold in the dental field is known from the German OLS 30 42 008.

SUMMARY OF THE INVENTION

Accordingly, an object of the present invention is to create a dental-filling material from a gold-alloy powder and which can also contain an organic binder for insertion into dental cavities by gold-condensation techniques, whereby hardnesses exceeding 100 HV can be achieved. In addition, another object of the invention is to provide a method for preparing dental-filling material.

In achieving the above and other objects, one feature of the invention resides in incorporating into the gold-alloy powder selected metals as the alloying components. The alloying components lead to hardening gold-alloys while simultaneously being soluble in nitric acid. Another feature of the invention resides in that the surface layer of the gold-alloy powder consists of pure gold and is roughened.

Preferably the alloying components of the gold-alloy powder are present in an amount up to 50% of one or more precious metals from the group consisting of palladium and silver and one or more of the base metals zinc, copper, indium and gallium.

Advantageously the film thickness of the gold layer on the gold-alloy powder particles falls between 0.1 and 2 $\mu$m, especially between 0.5 and 1.5 $\mu$m.

Furthermore the gold-alloy powder can be made to assume a pasty consistency by means of an organic plastic binder liquefying between 20° and 45° C. A suitable organic plastic binder with these characteristics can be used, e.g., as shown in the prior art mentioned above. The dental-filling material is prepared in accordance with the invention that gold-alloy powders of the proper compositions are made to harden by heat treatment and then a roughened surface layer of pure gold free of the alloying metals is achieved by operation of nitric acid.

The treatment in nitric acid preferably is carried out at elevated temperature until a gold layer free of alloying metals and 0.1 to 2 $\mu$m thick has been formed.

The gold powder so prepared combines the hardness of the hardened gold-alloy powder particles with the easy fusing of pure gold. In this manner hardnesses from 100 to 120 HV can be achieved, whereby this dental-filling material also is particularly applicable for use in situations where strong stresses are to be expected.

All metals leading to a hardening gold-alloy are suitable as alloying components for purposes of this invention. Long series of such metal combinations are known in the art for dental gold alloys. Preferably those gold alloys are used that contain palladium and possibly silver as the main alloying component, and additionally a base metal selected from the group consisting of zinc, copper, indium and gallium, and mixtures of such base metals.

DETAILED EMBODIMENTS OF THE INVENTION

The Examples below serve to illustrate the preparation and the composition of such dental-filling materials of this invention:

EXAMPLE 1

A gold alloy of 35% silver, 10% palladium and 5% zinc (balance gold) was pulverized in a wet-atomizer apparatus. A particle size fraction of equal to or less than 45 $\mu$m was separated and was ground in alcohol for 1 hour in a ball mill. A flake powder is obtained in this manner which was hardened by tempering for 15 minutes at 800° C. in an inert gas atmosphere. It was then quenched and then was made to age artificially for 15 minutes at 400° C. Thereupon this powder was treated for 6 hours in boiling nitric acid, whereby a pure gold surface layer about 1 $\mu$m thick free of alloying metal was obtained. Following washing and drying, a highly active powder of low friability was obtained, which was compacted in a model-cavity and reached a hardness of 115 HV.

EXAMPLE 2

A gold alloy with 18.5% silver, 11% palladium and 3.5% indium content was processed in the same manner of Example 1. The hardness of the test filling was 105 HV.

EXAMPLE 3

A gold alloy with 25% silver, 8% palladium, 11.5% copper and 0.5% zinc was processed in the same manner of Example 1. A filling with a hardness of 110 HV is obtained.

Further variations and modifications of the foregoing will be apparent to those skilled in the art and are intended to be encompassed by the claims appended hereto.

German priority application P 38 04 022.0-42 is relied on and incorporated herein by reference.

What is claimed is:

1. A dental-filling material comprising a gold-alloy powder for filling dental cavities by gold condensation, said gold-alloy powder being formed of gold and at least one metal capable of alloying with gold to produce a hard gold alloy and which metal is soluble in nitric acid, the surface layer of said gold-alloy powder being rough and consisting of pure gold.

2. The dental-filling material according to claim 1 which additionally contains an organic binder.

3. The dental-filling material according to claim 1, wherein said gold-alloy powder contains a total of up to 50% of one or more precious metals from the group consisting of palladium and silver and one or more of the base metals from the group consisting of zinc, copper, indium and gallium.

4. The dental-filling material according to claim 3 which additionally contains an organic binder.

5. The dental-filling material according to claim 1, wherein the thickness of the surface gold layer on the gold-alloy powder is between 0.1 and 2 microns.

* * * * *